(12) United States Patent
Johnson et al.

(10) Patent No.: US 8,187,573 B2
(45) Date of Patent: May 29, 2012

(54) IN VIVO DETECTION OF APOPTOSIS

(75) Inventors: Gary L. Johnson, Bloomington, MN (US); Brian W. Lee, Minnetonka, MN (US)

(73) Assignee: Immunochemistry Technologies, LLC, Bloomington, MN (US)

( * ) Notice: Subject to any disclaimer, the term of this patent is extended or adjusted under 35 U.S.C. 154(b) by 757 days.

(21) Appl. No.: 12/091,031

(22) PCT Filed: Oct. 12, 2006

(86) PCT No.: PCT/US2006/040047
§ 371 (c)(1),
(2), (4) Date: Sep. 15, 2008

(87) PCT Pub. No.: WO2007/050319
PCT Pub. Date: May 3, 2007

(65) Prior Publication Data
US 2009/0142260 A1 Jun. 4, 2009

Related U.S. Application Data

(60) Provisional application No. 60/729,227, filed on Oct. 21, 2005.

(51) Int. Cl.
*A61K 49/00* (2006.01)
(52) U.S. Cl. ...... 424/9.2; 424/1.11; 424/1.65; 424/1.81; 424/1.85; 424/1.89
(58) Field of Classification Search .................. 424/1.11, 424/1.49, 1.65, 1.73, 1.81, 1.85, 1.89, 9.1, 424/9.2, 9.3, 9.4, 9.5, 9.6, 9.7, 9.8
See application file for complete search history.

(56) References Cited

U.S. PATENT DOCUMENTS

| | | | |
|---|---|---|---|
| 6,153,591 A | 11/2000 | Cai et al. | |
| 6,197,278 B1 | 3/2001 | Blankenberg et al. | |
| 6,348,185 B1 | 2/2002 | Piwnica-Worms | |
| 6,511,430 B1 | 1/2003 | Sherar et al. | |
| 6,589,503 B1 | 7/2003 | Piwnica-Worms | |
| 6,756,207 B1 * | 6/2004 | Giuliano et al. | 435/7.2 |
| 7,056,947 B2 | 6/2006 | Powers et al. | |
| 2005/0244812 A1 | 11/2005 | Ziv et al. | |
| 2005/0276750 A1 | 12/2005 | Ziv et al. | |
| 2006/0275215 A1 | 12/2006 | Hiscock et al. | |

FOREIGN PATENT DOCUMENTS

| | | |
|---|---|---|
| WO | WO 01/89584 | 11/2001 |
| WO | WO 03/058194 | 7/2003 |
| WO | WO 03/059877 | 7/2003 |
| WO | WO 03/060466 | 7/2003 |
| WO | WO 2004/002401 | 1/2004 |
| WO | WO 2004/069773 | 8/2004 |
| WO | WO 2005/035497 | 4/2005 |
| WO | WO 2005/053752 | 6/2005 |

OTHER PUBLICATIONS

Feng et al, Chin. Ophthal. Res., Oct. 2006, vol. 24, No. 5, pp. 468-471.*
Bedner, E., et al., "Activation of caspases measured in situ by binding of fluorochrome-labeled inhibitors of caspases (FLICA): correlation with DNA fragmentation", *Exp. Cell Res. 259*, 308-313, (2000).
Belhocine, T., et al., "The imaging of apoptosis with the radiolabeled annexin V: optimal timing for clinical feasibility", *Technol. Cancer Res. Treat.*, 3(1), 23-32, (2004).
Boersma, H.H., et al., "Past, present, and future of annexin A-5: from protein discovery to clinical applications", *J. Nucl. Med.*, 46(12), 2035-2050, (2005).
Campbell, D.A. and A. K. Szardenings, "Functional profiling of the proteosome with affinity labels", *Current Opinion*, 7, 296-303, (2003).
Corsten, M.F., et al., "Counting heads in the war against cancer: defining the role of annexin A5 imaging in cancer treatment and surveillance", *Cancer Res.*, 66, 1255-1260, (2006).
Cursio, R., et al., "Liver apoptosis following normothermic ischemia-reperfusion: in vivo evaluation of caspase activity by FLIVO assay in rats", *Transplantation Proceedings*, 40, 2038-2041, (2008).
Cursio, R., et al., "Tyrosine phosphorylation of insulin receptor substrates during ischemia/reperfusion-induced apoptosis in rat liver", *Langenbecks Arch. Surg.*, 394, 123-131, (2009).
Delgado-Martin, C., et al., "A protocol to detect apoptotic dendritic cells in murine lymph nodes using multiphoton microscopy", *Nature Protocols*, DOI: 10.1038/nprot.2009.133, 4 pages, (2009).
Dicker, D.T., et al., "Heterogeneity in non-invasive detection of apoptosis among human tumor cell lines using annexin-V tagged with EGFP or Qdot-705", *Cancer Biol. Ther.*, 9, 1014-1017, (2005).
Dillon, S.R., et al., "Annexin V binds to positively selected B cells", *J. of Immunol.*, 166, 58-71, (2001).
Ekici, O.D., et al., "Aza-peptide Michael acceptors: a new class of inhibitors specific for caspases and other clan CD cysteine proteases", *J. Med. Chem.*, 47(8), 1889-1892, (2004).
Erman, A., et al., "Apoptosis and desquamation of urothelial cells in tissue remodeling during rat postnatal development", *J. Histochem. Cytochem.*, 57, 721-730, (2009).
Escribano, C., et al., "CCR7-Dependent Stimulation of Survival in Dendritic Cells Involves Inhibition of GSK3", *The Journal of Immunology*, 183, 6282-6295, (2009).
Griffin, R.J., et al., "Use of a fluorescently labeled poly-caspase inhibitor for in vivo detection of apoptosis related to vascular-targeting agent arsenic trioxide for cancer therapy", *Technology in Cancer Research and Treatment*, 6, 651-654, (2007).
Haberkorn, U., et al., "Investigation of a potential scintigraphic marker of apoptosis: radioiodinated Z-Val-Ala-DL-Asp(*O*-methyl)-fluoromethyl ketone", *Nuclear Medicine and Biology*, 28, 793-798, (2001).

(Continued)

*Primary Examiner* — D L Jones
(74) *Attorney, Agent, or Firm* — Viksnins Harris & Padys PLLP

(57) ABSTRACT

The invention provides methods and products, such as kits, useful for determining the apoptotic state of cells in an organism, comprising detecting the presence or abundance of at least one caspase affinity labeling agent in the cells of an animal into which at least one caspase affinity labeling agent has been introduced, wherein the presence or abundance of the caspase affinity labeling agent correlates with the apoptotic state of the cells.

23 Claims, 5 Drawing Sheets

OTHER PUBLICATIONS

Kietselaer, B.L., et al., "The role of labeled Annexin A5 in imaging of programmed cell death. From animal to clinical imaging", *Q. J. Nucl. Med.*, 47(4), 349-361, (2003).

Krantz, A., et al., "Peptidyl (acyloxy)methyl ketones and the quiescent affinity label concept: the departing group as a variable structural element in the design of inactivators of cysteine proteinases", *Biochemistry*, 30(19), 4678-4687, (1991).

Laxman, B., et al., "Noninvasive real-time imaging of apoptosis", *Proc. Natl. Sci. Acad. USA*, 99(26), 16551-16555, (2002).

Medina, M.A., et al., "A high-throughput model for fat graft assessment", *Lasers in Surg Med.*, 41, 738-744, (2009).

Messerli, S.M., et al., "A novel method for imaging apoptosis using a caspace-1 near-infrared fluorescent probe", *Neoplasia*, 6(2), 95-105, (Mar./Apr. 2004).

Nicholson, D.W., "Caspase structure, proteolytic substrates, and function during apoptotic cell death", *Cell Death and Differ.*, 6, 1028-1042, (1999).

Reddy, G.K., "Noninvasive visualization of apoptosis using radiolabeled annexin V could predict response to chemotherapy", *Clin. Lung Cancer*, 7(3), 166-167, (2005).

Riol-Blanco, L., et al., "Immunological synapse formation inhibits, via NF-kappaB and FOXO1, the apoptosis of dendritic cells", *Nat. Immunol.*, 10(7), 753-760 and 2 supplemental pages, (2009).

Slatter, T.L., et al., "p53-mediated apoptosis prevents the accumulation of progenitor B cells and B-cell tumors", *Cell Death and Differentiation*, 17, 540-550, (2010).

Smolewski, P., et al., "Detection of caspases activation by fluorochrome-labeled inhibitors: Multiparameter analysis by laser scanning cytometry", *Cytometry*, 44, 73-82, (2001).

Smolewski, P., et al., "Kinetics of HL-60 cell entry to apoptosis during treatment with TNF-α or camptothecin assayed by the stathmo-apoptosis method", *Cytometry*, 47, 143-149, (2002).

Thornberry, N.A., et al., "Inactivation of interleukin-1beta converting enzyme by peptide (acyloxy) methyl ketones", *Biochemistry*, 33, 3934-3940. (1994).

Tsai, Y.C., et al., "The ubiquitin ligase gp78 promotes sarcoma metastasis by targeting KAI1 for degradation", *Nature Medicine*, 13, 1504-1509, (2007).

Vanderheyden, J.L., et al., "Evaluation of $^{99m}$Tc-MAG$_3$-annexin V: influence of the chelate on in vitro and in vivo properties in mice", *Nucl. Med. Biol.*, 33(1), 135-144, (2006).

van der Most, R.G., et al., "Cyclophosphamide chemotherapy sensitizes tumor cells to TRAIL-dependent CD8 T cell-mediated immune attack resulting in suppression of tumor growth", *PLoS ONE*, 4, e6982, 1-11, (2009).

Watanabe, H., et al., "In vivo visualization of radiation-induced apoptosis using $^{125}$I-annexin V", *Nucl. Med. Commun.*, 27(1), 81-89, (2006).

Winssinger, N., et al., "Profiling protein function with small molecule microaarays", *Proc. Natl. Acad. Sci. USA*, 99(17), 11139-11144, (Aug. 2002).

Patent Cooperation Treaty, International Search Report & Written Opinion of the International Search Authority, PCT/US06/040047, Mar. 7, 2007, 16 pages.

Blankenberg, F.G., "Recent Advances in the Imaging of Programmed Cell Death", *Current Pharmaceutical Design*, 10, pp. 1457-1467, 2004.

Amstad, P.A. et al., "Detection of Caspase Activation In Situ by Fluorochrome-Labeled Caspase Inhibitors", *Bio Techniques 31*, pp. 608-616, 2001.

\* cited by examiner

Figure 1. SCK mammary tumor in A/J mice, Brightfield Image
Time: 0 hours
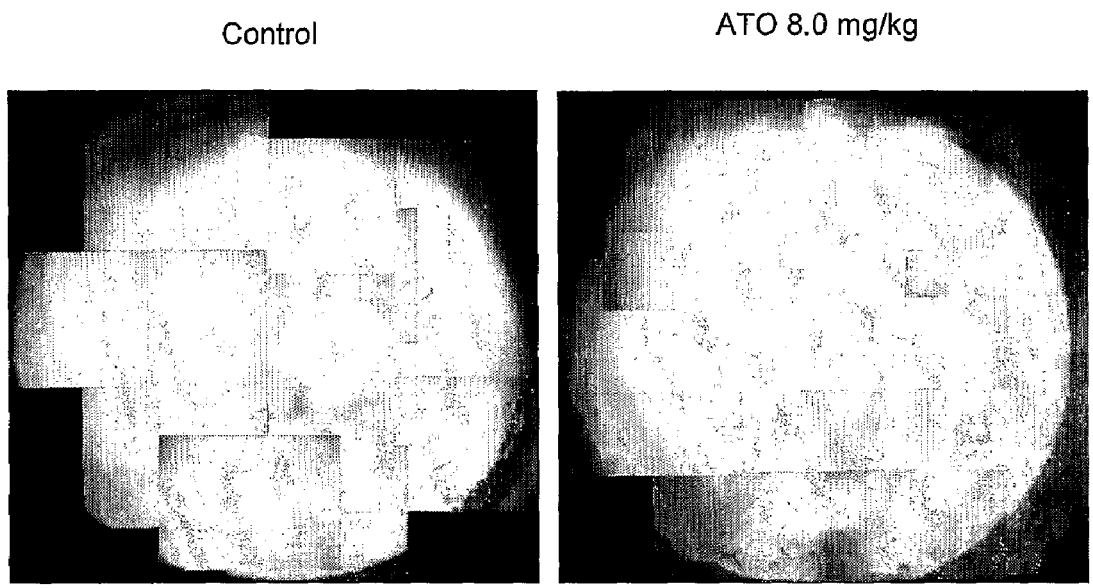
Figure 2. SCK mammary tumor in A/J mice, Brightfield Image
Time: 3 hours
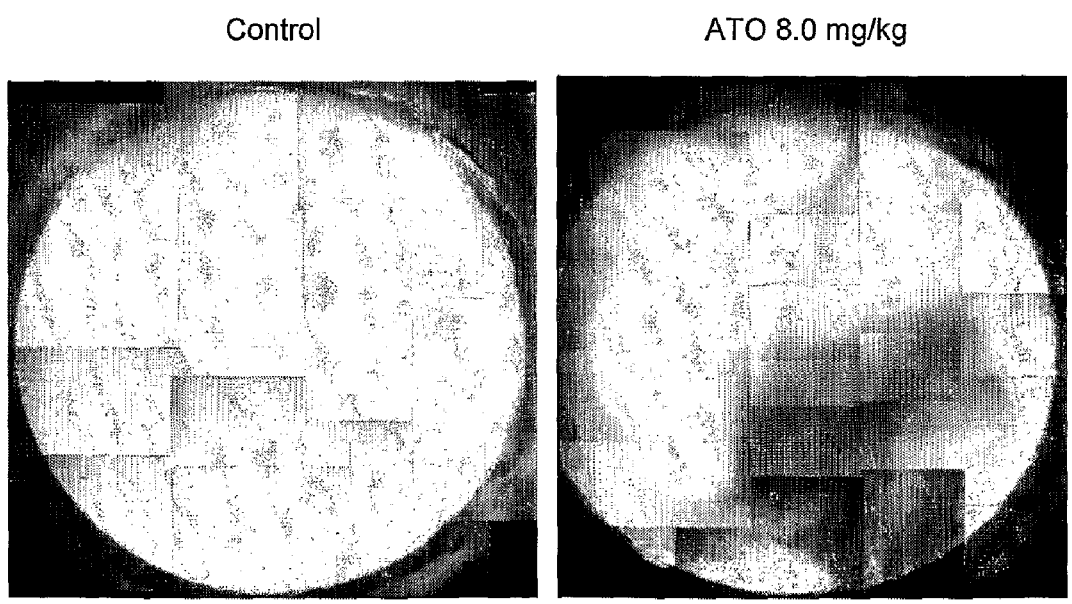

Figure 3. SCK mammary tumor in A/J mice, Brightfield Image, Time: 24 hours
Control                    ATO 8.0 mg/kg
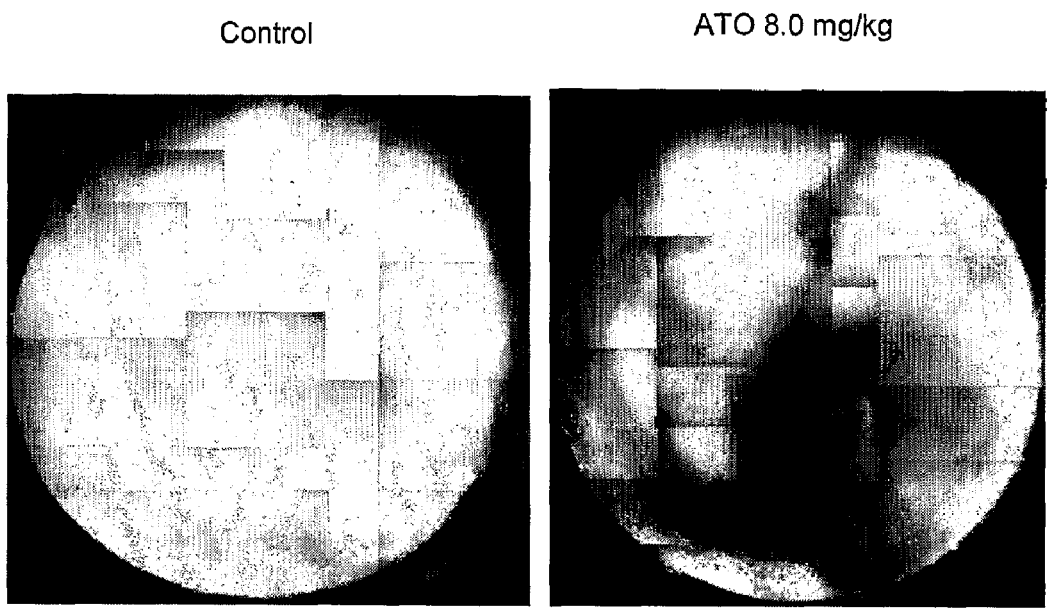
Figure 4. SCK mammary tumor in A/J mice, injected intravenously with 8.0 µg of FAM-VAD-FMK, 0 Hours
Post Treatment Time: 0 Hours, ATO 8.0 mg/kg
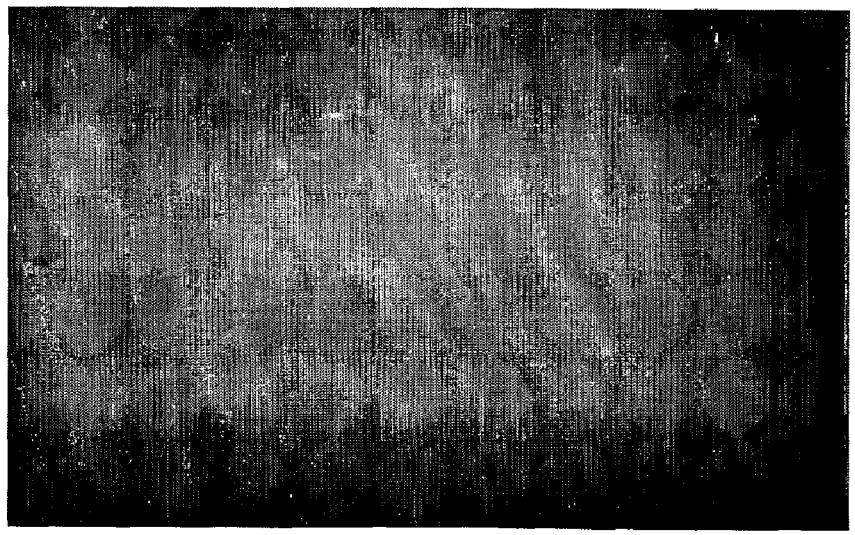

Figure 5. SCK mammary tumor in A/J mice, injected intravenously with 8.0 µg of FAM-VAD-FMK, 3 Hours
Post Treatment Time: 3 Hours, ATO 8.0 mg/kg
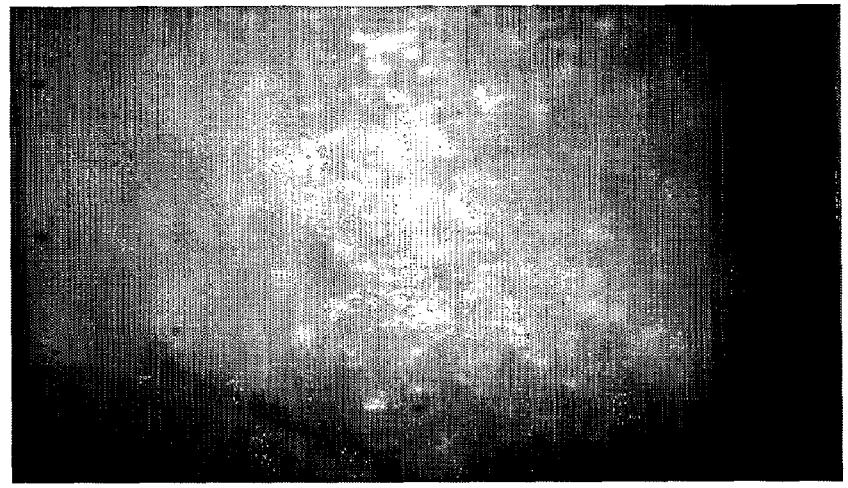
Figure 6. SCK mammary tumor in A/J mice, injected intravenously with 8.0 µg of FAM-VAD-FMK, 24 Hours
Post Treatment Time: 24 Hours, ATO 8.0 mg/kg
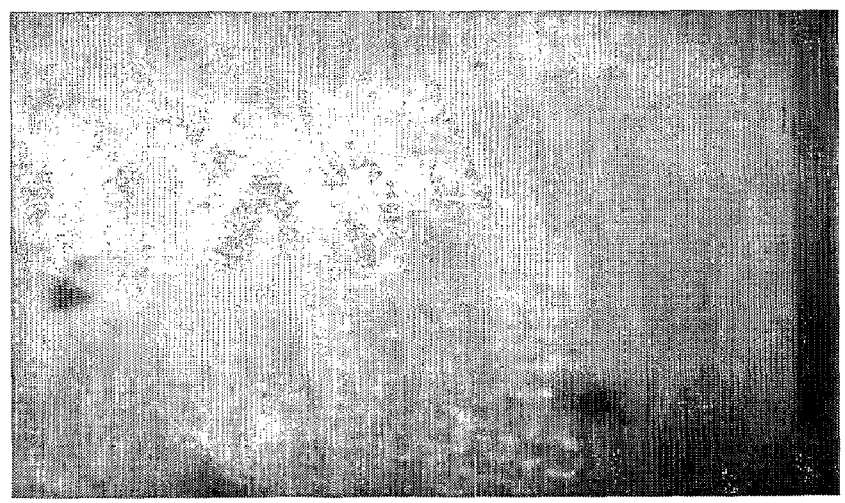

Figure 7. Confirmation by Flow Cytometry using excised tumor cells
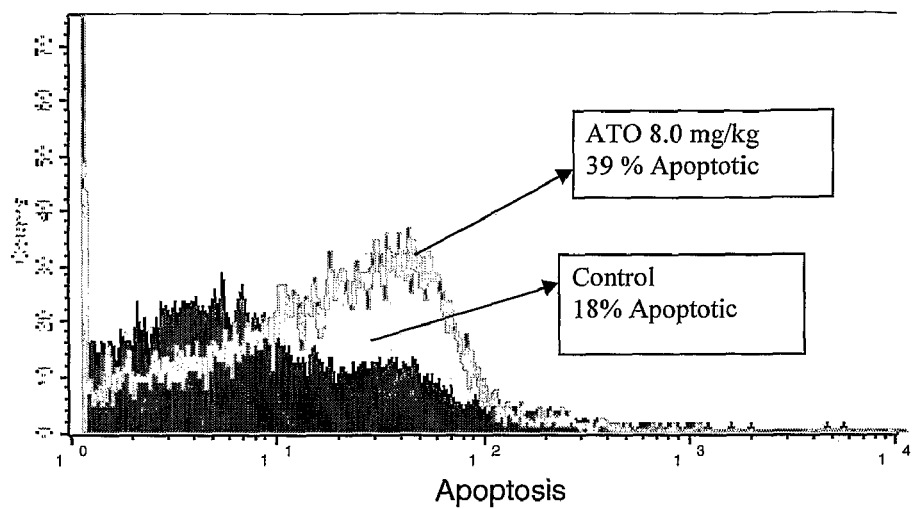
Figure 8. Longitudinal Study: Level of apoptosis in a tumor before treatment with ATO.
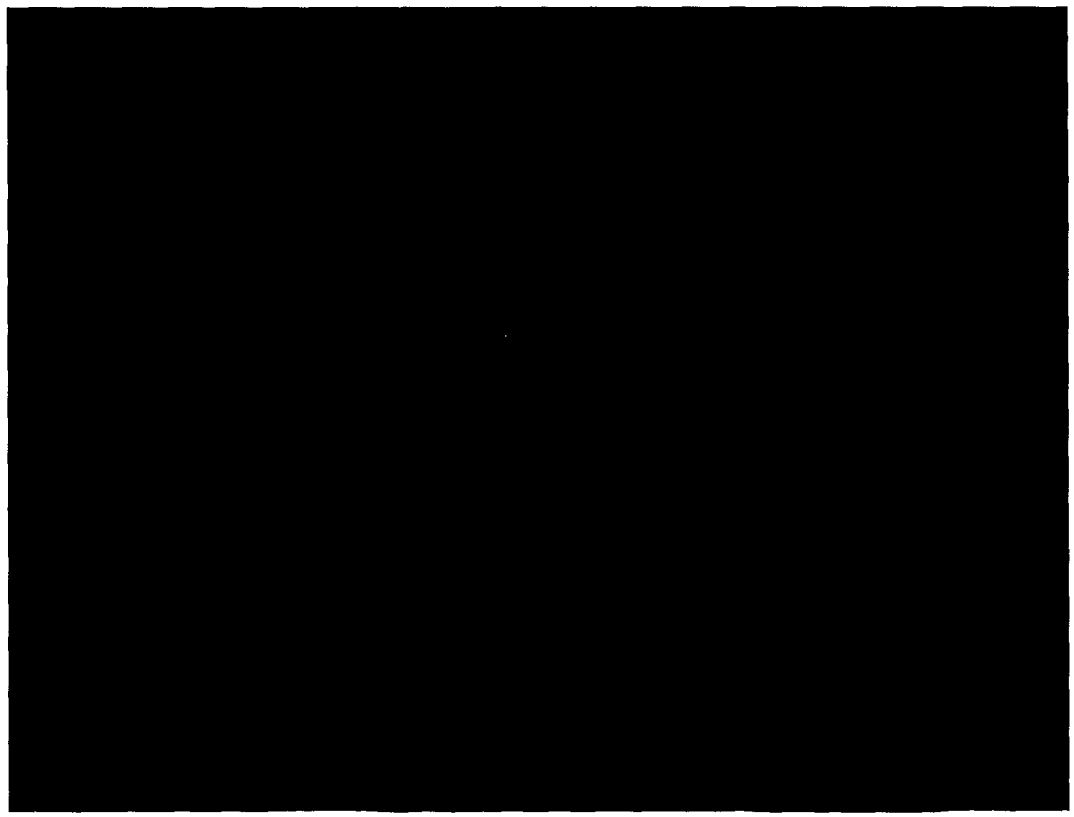

Figure 9. Longitudinal Study: Level of apoptosis in a tumor after 3 hours of treatment with ATO.
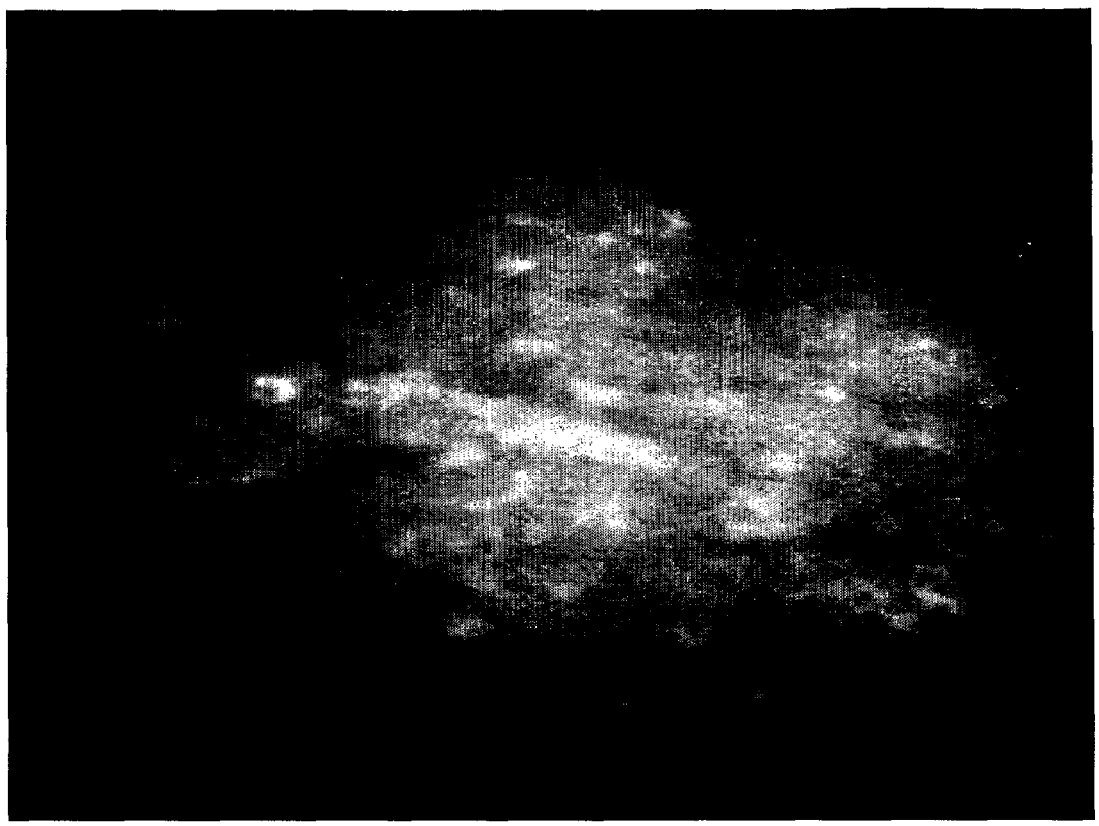

```
                        SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Asp Val Ala
1
```

IN VIVO DETECTION OF APOPTOSIS

RELATED APPLICATION(S)

This application is a National Stage application under 35 U.S.C. §371 and claims the benefit of International Application No. PCT/US2006/040047 having an International Filing Date of Oct. 12, 2006, which claims priority from U.S. Application No. 60/729,227, filed Oct. 21, 2005, which applications are herein incorporated by reference.

SEQUENCE LISTING

The instant application contains a Sequence Listing which has been submitted in ASCII format via EFS-Web and is hereby incorporated by reference in its entirety. Said ASCII copy, created on Jul. 14, 2011, is named 2043002U.txt and is 513 bytes in size.

BACKGROUND

There have been attempts at in vivo apoptosis detection and imaging using Annexin V and Annexin V derivatives (see, e.g., Kietselaer et al., 2003; Belhocine et al., 2004; Reddy, 2005; Boersma et al., 2005; Watanabe et al., 2006; Vanderheyden et al., 2006; and Corsten et al., 2006). Other attempts using novel compounds that rely on the perturbation and alterations of the normal organization of the cell plasma membrane have also been attempted (see, e.g., U.S. Patent Application Publications 2005/0244812 and 2005/0276750).

None of the previously described methods uses a cell permeant probe for the detection and imaging of apoptosis. As a result of this and other issues, all of the aforementioned methods have been plagued with problems resulting in high backgrounds and lack of binding to certain apoptotic tumor cells. Annexin V is not cell permeant, is slow to penetrate any tissues, has high background, and does not detect early apoptotic cells (Kietselaer et al, 2003; Belhocine et al., 2004; Boersma et al., 2005; Watanabe et al., 2006; Vanderheyden et al., 2006, and Corsten et al, 2006). Leading to high background, Annexin V binds positively to normal and healthy bone marrow derived cells (Dillon, 2001). It has been reported that Annexin V does not bind to all tumor cells (Dicker, 2005).

In the Ziv publications (U.S. Patent Application Publications 2005/0244812 and 2005/0276750), it is reported that their compounds accumulate in apoptotic cells at a rate faster than they accumulate in cells that are not undergoing cell wall turnover. This leads to high background levels and lack of specificity similar to Annexin V. Requiring a compromised cell state also prohibits the detection of cells that are in the early stages of apoptosis.

Thus, previously described methods of in vivo apoptosis detection and imaging lack specificity and sensitivity and are subject to high background. The use of sensitive and specific cell permeant inhibitor probes that bind to specific active enzymes and proteases involved in apoptosis has not been described.

Thus, methods and products for in vivo determination of the apoptotic state of cells in an organism are needed.

BRIEF DESCRIPTION OF THE FIGURES

FIG. 1. Low magnification bright-field image composite of SCK mammary tumors taken through a window chamber. Each mouse was injected with 2×10$^5$ SCK tumor cells. The tumors were allowed to grow for 7 days. A low level of hemorrhaging was seen in both control and test mice.

FIG. 2. Low magnification bright-field image composite of SCK mammary tumors taken through a window chamber. The control mouse was injected with a placebo and the test mouse was injected with 8.0 mg/kg of arsenic trioxide (ATO). Increased levels of hemorrhaging can be seen in the mouse that received the ATO treatment. The photographs were taken 3 hours after completion of treatment.

FIG. 3. Low magnification bright-field image composite of SCK mammary tumors taken through a window chamber. The control mouse was injected with a placebo and the test mouse was injected with 8.0 mg/kg of ATO. Increased levels of hemorrhaging can be seen in mice that received the ATO treatment, the amount of hemorrhaging has also increased over time when compared to the 3 hour post treatment photograph. The photographs were taken 24 hours after completion of treatment.

FIG. 4. High magnification photograph using an excitation at 488 nm with a fluorescein filter to detect fluorescence. The mouse was injected with 2×10$^5$ SCK tumor cells. The tumor was allowed to grow for 7 days. The mouse was then injected intravenously (I.V.) through the tail vein with 8 μg of the apoptosis detection reagent FAM-VAD-FMK prior to therapeutic treatment. The reagent was allowed to circulate in the mouse for 30 minutes before photographing with 488 nm excitation. The results demonstrate a low level of apoptosis which is expected in a fast growing SCK tumor.

FIG. 5. High magnification photograph using an excitation at 488 nm with a fluorescein filter to detect fluorescence. The mouse was injected with 8.0 mg/kg of ATO. After 3 hours post ATO treatment, the mouse was injected intravenously through the tail vein with 8 μg of FAM-VAD-FMK. The reagent was allowed to circulate in the mouse for 30 minutes before photographing with 488 nm excitation. The results demonstrate a high level of apoptosis.

FIG. 6. High magnification photograph using an excitation at 488 nm with a fluorescein filter to detect fluorescence. The mouse was injected with 8.0 mg/kg of ATO. After 24 hours post ATO treatment, the mouse was injected intravenously through the tail vein with 8 μg of FAM-VAD-FMK. The reagent was allowed to circulate in the mouse for 30 minutes before photographing with 488 nm excitation. The results demonstrate a higher level of apoptosis.

FIG. 7. Each mouse was injected with 2×10$^5$ SCK tumor cells. The tumors were allowed to grow for 7 days. The control mouse was injected with a placebo and the test mouse was injected with 8.0 mg/kg of ATO. After 24 hours of treatment the mice were injected intravenously through the tail vein with 8 μg of FAM-VAD-FMK. The reagent was allowed to circulate in the mouse for 30 minutes before excising the tumors. The tumors were then broken apart and the cells were dispersed. The cells were then analyzed by flow cytometry. Flow cytometry analysis demonstrated that the treated mouse had an apoptosis induction rate of 39% while the control mouse had an apoptosis induction rate of only 18%.

FIG. 8. Apoptosis imaging of FSaII tumor in DSFC in a nu/nu mouse. 10× capture of apoptosis prior to ATO injection, 45 minutes after 12.0 μg of FAM-VAD-FMK were injected intravenously through the tail vein. Very little apoptosis is visible.

FIG. 9. Same tumor as in FIG. 8. 10× capture of apoptosis 3 hours post ATO (8.0 mg/kg) injection. 45 minutes after 12.0 μg of FAM-VAD-FMK were injected intravenously through the tail vein. The increase in apoptosis within the tumor is clear.

SUMMARY OF CERTAIN EMBODIMENTS OF THE INVENTION

Accordingly, certain embodiments of the invention provide methods and products, such as kits, useful for determining the apoptotic state of cells in vivo, such as in an organism such as an animal.

This invention provides cell permeant probes that bind specifically to up-regulated caspase and apoptosis-associated enzymes, which allows for the detection and imaging of apoptosis events in vivo.

Certain embodiments of the invention provide a method for in vivo determination of the apoptotic state of one or more cells in an animal, including detecting the presence or abundance of at least one caspase affinity labeling agent in the cells of an animal into which at least one caspase affinity labeling agent has been introduced, wherein the presence or abundance of the caspase affinity labeling agent correlates with the apoptotic state of the cells.

Certain embodiments of the invention provide a method for in vivo determination of whether a therapeutic agent modulates apoptosis in one or more cells in an animal, including detecting the presence of at least one caspase affinity labeling agent in the cells of an animal that has been previously treated with the therapeutic agent and into which at least one caspase affinity labeling agent has been introduced, wherein the presence of the caspase affinity labeling agent correlates with the ability of the therapeutic agent to modulate apoptosis. In certain embodiments of the invention, the method determines whether the therapeutic agent increases or decreases apoptosis.

Certain embodiments of the invention provide a method for in vivo determination of whether a radiation treatment modulates apoptosis in one or more cells in an animal, including detecting the presence of at least one caspase affinity labeling agent in the cells of an animal into which at least one caspase affinity labeling agent has been introduced, wherein the animal has been previously treated with radiation, wherein the presence of the caspase affinity labeling agent correlates with the ability of the radiation to modulate apoptosis. In certain embodiments of the invention, the method determines whether the radiation treatment increases or decreases apoptosis.

Certain embodiments of the invention provide an in vivo diagnostic method for determining the presence or absence of a disease characterized by the presence of apoptosis including detecting the presence of at least one caspase affinity labeling agent in the cells of the animal into which at least one caspase affinity labeling agent has been introduced, wherein the presence or absence of the at least one caspase affinity labeling agent correlates with the presence or absence of the disease.

In some embodiments of the invention, the diseases include but are not limited to eye disease such as glaucoma, retinal diseases such as macular degeneration and proliferative retinopathy; neurodegenerative diseases such as neuropathy, Alzheimer's disease, multiple sclerosis, Huntington's disease and others; and cardiac disease.

Certain embodiments of the invention provide an in vivo method for evaluating the sensitivity of a disease to at least one therapeutic agent or treatment, including detecting the presence or abundance of at least one caspase affinity labeling agent in the cells of an animal into which at least one caspase affinity labeling agent has been introduced, wherein the animal has previously received the therapeutic agent or treatment, wherein the presence or abundance of the caspase affinity labeling agent correlates with the sensitivity of the disease to the at least one therapeutic agent or treatment.

Certain embodiments of the invention provide a method for the monitoring of cancer treatment in an animal, including: detecting the presence or abundance of at least one caspase affinity labeling agent in the cells of the animal into which at least one caspase affinity labeling agent has been introduced that has received a therapeutic agent or treatment, wherein the presence or abundance of at least one caspase affinity labeling agent correlates with the efficacy of the therapeutic agent or treatment.

Certain embodiments of the invention provide a method for the monitoring of leukemia treatment in an animal, including detecting the presence or abundance of at least one caspase affinity labeling agent in the cells of the animal into which at least one caspase affinity labeling agent has been introduced that has received a therapeutic agent or treatment, wherein the presence or abundance of at least one caspase affinity labeling agent correlates with the efficacy of the therapeutic agent or treatment.

Certain embodiments of the invention provide a method for the monitoring of blood and bone marrow disease treatment in an animal including detecting the presence or abundance of at least one caspase affinity labeling agent in the cells of an animal into which at least one caspase affinity labeling agent has been introduced that has received a therapeutic agent or treatment, wherein the presence or abundance of at least one caspase affinity labeling agent correlates with the efficacy of the therapeutic agent or treatment.

Certain embodiments of the invention provide a method for determining if one or more compounds within a chemical library modulate caspase activity in an animal including determining the level of at least one caspase affinity labeling agent in cells of an animal into which at least one caspase affinity labeling agent has been introduced, wherein the animal has been contacted with one or more compounds from the library, and determining whether the one or more compounds modulate the caspase activity.

Certain embodiments of the invention provide a method for determining if one or more compounds within a chemical library modulate apoptosis in an animal including determining the level of at least one caspase affinity labeling agent in cells of an animal into which at least one caspase affinity labeling agent has been introduced, wherein the animal has been contacted with one or more compounds from the library, and determining whether the one or more compounds modulate apoptosis.

In certain embodiments of the invention, the determination step includes comparing the level of affinity labeling agent in the animal with a control animal not exposed to the compound.

In certain embodiments, the determination step is a longitudinal study that is comprised of a comparison of the level of affinity labeling agent in the animal before exposure to the compound and after the animal has been exposed to the compound. In this case the animal is contacted with the affinity labeling agent before exposure to the compound and a second time, after exposure to the compound.

In certain embodiments of the invention, detection is carried out using NMR, MRI, CT, CAT, or PET scans; a flow cytometer; a laser scanning cytometer; a fluorescence microplate reader; a luminescence microplate reader, a chromogenic microplate reader; a fluorescence microscope; a confocal microscope; a luminescence microscope, or scintigraphy; a bright-field microscope; a whole animal fluorescence imaging systems (optical imaging system); or a whole animal luminescence imaging system, or a combination thereof.

In certain embodiments of the invention, detection is carried out using a Window Chamber inserted into the animal.

In certain embodiments of the invention, detection is carried out using a fluorescence microscope; a confocal microscope; a bright-field microscope, or luminescence microscope.

In certain embodiments of the invention, detection is carried out or confirmed by removing a sample from the animal such as by extraction, biopsy, venipuncture, dissection, or other suitable methods and detection is carried out on a sample that has been removed from the animal.

In certain embodiments of the invention, detection is via a flow cytometer; a laser scanning cytometer; a fluorescence microplate reader; a chromogenic microplate reader; a fluorescence microscope; a confocal microscope; a bright-field microscope; a luminescence microplate reader; or a luminescence microscope.

In certain embodiments of the invention, the presence or abundance of the affinity labeling agent is detected in the bone marrow, thymus, lymph nodes, spleen or circulating blood of the animal.

In certain embodiments of the invention, the presence or abundance of the affinity labeling agent is detected in peripheral blood monocytes (PBMCs).

In certain embodiments of the invention, the cells are included in tissues, organs or tumors of the animal.

In certain embodiments of the invention, the caspase affinity labeling agent is introduced into the animal by intravenous, intravascular, intraperitoneal, intravitreal, intraocular, intracranial, intrapleural, intrathoracic, intramuscular, intrapulmonary, injection, perfusion, or lavage administration.

As used herein, the term animal refers to any type of living organism, e.g., a multi-cellular organism. In certain embodiments of the invention, the animal is a mammal. In certain embodiments of the invention, the mammal is a human male or female.

Certain embodiments of the invention provide an assay kit including packaging materials and one or more caspase affinity labeling agents and instructions for using the caspase affinity labeling agents to determine the level of apoptosis in vivo.

In certain embodiments of the invention, the caspase affinity labeling agent is a cell permeant probe consisting of a compound of formula I:

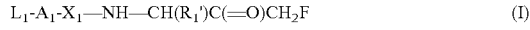

$$L_1\text{-}A_1\text{-}X_1\text{—NH—}CH(R_1')C(=O)CH_2F \qquad (I)$$

wherein:

$L_1$ is a detectable group that may comprise gadolinium (Gd), Terbium (Tb), Europium (Eu) or any other Lanthanide series element (e.g., Ce, Pr, Nd, Pm, Sm, Dy, Ho, Er, Tm, Yb, or Lu) or Iron (Fe), Manganese (Mn), Rhenium (Re), or Technetium (Tc). The detectable group may be suitable for nuclear magnetic resonance (NMR) or magnetic resonance imaging (MRI) detection, or luminescence or scintigraphy. The detectable group may be iodine (I) or barium (Ba), e.g., for computer tomography (CT scan) or computer axial tomography (CAT scan) detection. The detectable group may be a positron emitter (such as $^{11}C$, $^{13}N$, $^{15}O$ or $^{64}Cu$), e.g., for positron emission tomography (PET scan). The detectable group may be a fluorescent label (e.g., a fluorescein derivative, sulforhodamine derivative, Cy dye derivative, BODIPY derivative, coumarin derivative, Quantum Dot, or any fluorescent dye that can be attached, e.g., to an amino group, directly or by linkers). The detectable group may be a radioisotope (e.g. $^3H$, $^{14}C$, or $^{35}S$).

$A_1$ is a direct bond or a linker that can simply be a covalent bond. The detectable group may be attached directly, e.g., to the N-terminal amino group of the peptide or amino acid (e.g., amide linkage L-(C=O)—NH—R). $A_1$ can also be any member of the class of linkers well known to the art. Linkers are typically about 4-18 atoms long, including carbon, nitrogen, oxygen or sulfur atoms;

$X_1$ is absent, an amino acid, or a peptide which may be a peptide having about 1 to 10 amino acids, e.g., about 2 to 4 amino acids (e.g., V, VA, YVA, DEV, LEE, LEH, VDVA (SEQ ID NO: 1), IET, WHE or AEV). For a compound of formula (I), $X_1$ may be a natural amino acid (e.g., A, V, or E). For a compound of formula (I), $R_1'$ may be a methylene carboxy (ethanoic) side-chain ($CH_2$—COOH) as caspases typically have an aspartate in the $P_1$ position of the peptide substrate.

$R_1'$ may be an aspartic acid side-chain ($CH_2$—COOH) or an ester of aspartic acid (e.g., —$CH_2CO_2R$, where R is $C_1$-$C_6$ alkyl or benzyl, $CH_3$, $C_2H_5$ or $CH_2C_6H_5$), for example. Certain caspase affinity labeling probes may contain the same labels and a 1 to 5 amino acid sequence, but utilize an aza-peptide epoxide modification of the aspartic acid (see, e.g., U.S. Pat. No. 7,056,947 B2), or an aza-peptide Michael acceptor (Ekici et al., 2004), an aldehyde modification of the aspartic terminal carboxyl group (HC=O), a chloromethyl ketone group ($CH_2Cl$), or an acyloxy reactive group ((C=O)O—Ar, where Ar is [2,6-$(CF_3)_2$]benzoate or various derivative of same (Krantz et al., 1991, and Thornberry et al., 1994).

DETAILED DESCRIPTION

Certain embodiments of the invention provide methods and products, such as kits, useful for determining the apoptotic state of cells in an organism such as a human.

In some embodiments, the invention provides a method for in vivo determination of the apoptotic state of one or more cells (e.g., viable whole cells), which may, e.g., be included in tissues, organs or tumors, in mammals such as humans, including: 1) contacting the cells in vivo with at least one caspase affinity labeling agent that is introduced into the subject, e.g., by intravenous, intravascular, intraperitoneal, intravitreal, intraocular, intracranial, intrapleural, intrathoracic, intramuscular, intrapulmonary, injection, perfusion, or lavage administration; and 2) detecting the presence or abundance of at least one affinity labeling agent in the cells; wherein the presence or abundance of the caspase affinity labeling agent correlates with the apoptotic state of the cells.

In some embodiments of the invention, the caspase affinity labeling agent is a cell permeant probe. It is believed that the caspase affinity labeling agent may inhibit active caspases by binding covalently to the active catalytic site and is retained within the cell. It is believed that these labeled membrane permeant probes penetrate the cell membrane of live cells and covalently bind to active caspase enzymes in apoptotic cells, thereby allowing for specific and sensitive detection of apoptosis (Bedner et al, 2000, Smolewski et al, 2001, and Smolewski et al., 2002). In certain embodiments of the invention, the caspase affinity labeling agent is a compound of formula I:

$$L_1\text{-}A_1\text{-}X_1\text{—NH—}CH(R_1')C(=O)CH_2F \qquad (I)$$

wherein:

L₁ is a detectable group that may comprise gadolinium (Gd), Terbium (Tb), Europium (Eu) or any other Lanthanide series element (e.g., Ce, Pr, Nd, Pm, Sm, Dy, Ho, Er, Tm, Yb, or Lu) or Iron (Fe), Manganese (Mn), Rhenium (Re), or Technetium (Tc). The detectable group may be suitable for nuclear magnetic resonance (NMR) or magnetic resonance imaging (MRI) detection, or luminescence or scintigraphy. The detectable group may be iodine (I) or barium (Ba), e.g., for computer tomography (CT scan) and computer axial tomography (CAT scan) detection. The detectable group may be a positron emitter (such as $^{11}$C, $^{13}$N, $^{15}$O, or $^{64}$Cu), e.g., for positron emission tomography (PET scan). The detectable group may be a fluorescent label (e.g., a fluorescein derivative, sulforhodamine derivative, Cy dye derivative, BODIPY derivative, coumarin derivative, Quantum Dot, or any fluorescent dye that can be attached, e.g., to an amino group, directly or by linkers. The detectable group may be a radioisotope (e.g. $^{3}$H, $^{14}$C, $^{35}$S).

$A^1$ is a direct bond or a linker that can simply be a covalent bond. The detectable group may be attached directly, e.g., to the N-terminal amino group of the peptide or amino acid (e.g., amide linkage L-(C=O)—NH—R). A, can also be any member of the class of linkers well known to the art. Linkers are typically about 4-18 atoms long, including carbon, nitrogen, oxygen or sulfur atoms.

$X_1$ is absent, an amino acid, or a peptide which may be a peptide having about 1 to 10 amino acids, e.g., about 2 to 4 amino acids (e.g., V, VA, YVA, DEV, LEE, LEH, VDVA (SEQ ID NO: 1), IET, WHE or AEV). For a compound of formula (I), $X_1$ may be a natural amino acid (e.g., A, V, or E). For a compound of formula (I), $R_1'$ may be a methylene carboxy (ethanoic) side-chain (CH₂—COOH) as caspases typically have an aspartate in the $P_1$ position of the peptide substrate.

$R_1'$ may be an aspartic acid side-chain (CH₂—COOH) or an ester of aspartic acid (e.g., —CH₂CO₂R, where R is $C_1$-$C_6$ alkyl or benzyl, CH₃, C₂H₅ or CH₂C₆H₅), for example. Certain caspase affinity labeling probes may contain the same labels and a 1 to 5 amino acid sequence, but utilize an aza-peptide epoxide modification of the aspartic acid (see, e.g., U.S. Pat. No. 7,056,947 B2), or an aza-peptide Michael acceptor (Ekici et al, 2004), an aldehyde modification of the aspartic terminal carboxyl group (HC=O), a chloromethyl ketone group (CH₂Cl), or an acyloxy reactive group ((C=O)O—Ar, where Ar is [2,6-(CF₃)₂]benzoate or various derivative of same (Krantz et al., 1991, and Thornberry et al., 1994).

The following structures are examples of compounds of formula I, but the invention is not limited to these structures. The term "reporter label" is used interchangeably with "detectable group".

One example is an Asp(OMe)-FMK modified reactive end that is believed to bind to the cysteine residue in the catalytic site of active caspases.

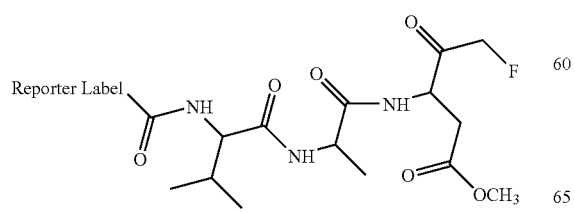

One example of a fluorescent labeled FMK caspase ligand is a carboxyfluorescein-valanyl-alanyl-aspartyl(O-methyl)-fluoromethyl ketone.

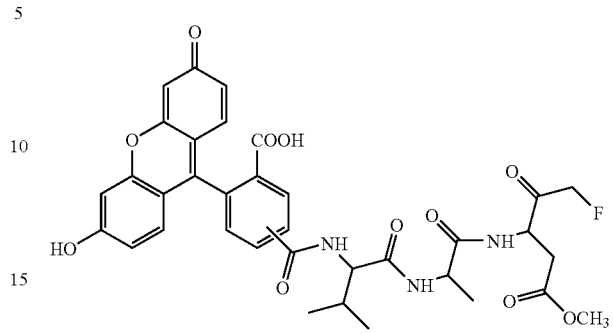

One example of a metal chelate labeled FMK caspase ligand is a Tc-valanyl-alanyl-aspartyl(O-methyl)-fluoromethyl ketone.

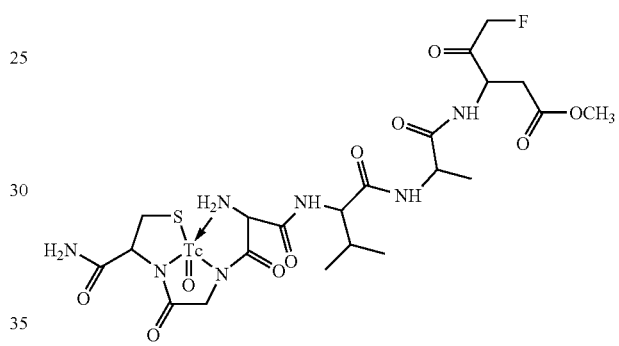

Once the fluoromethyl ketone peptides enter the cell and come into contact with an active caspase, it is believed that the sequence is recognized by the catalytic site and forms a covalent bond through a three step process. In the first step it is believed that the formation of a thiohemiketal intermediate occurs.

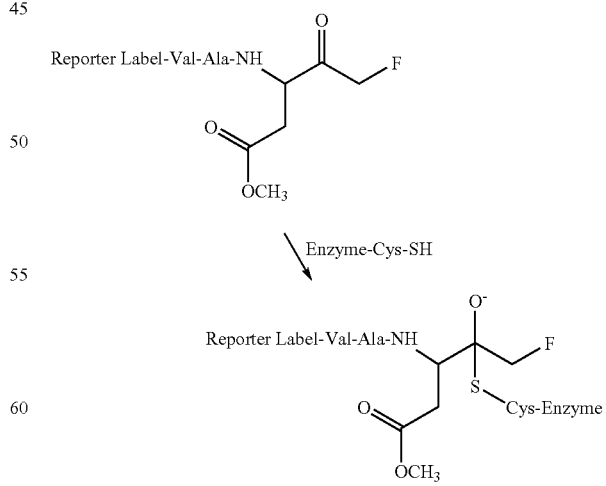

It is believed that the thiohemiketal intermediate undergoes a rearrangement to form a three membered sulfonium intermediate.

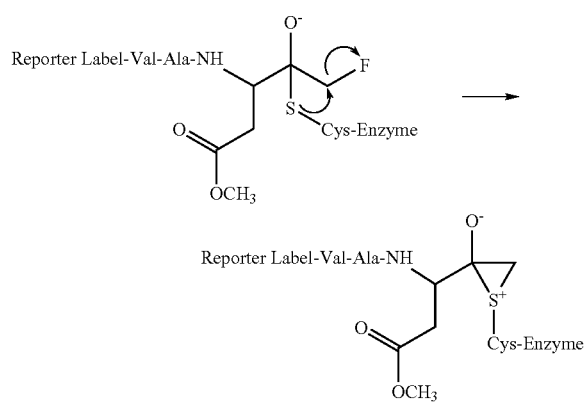

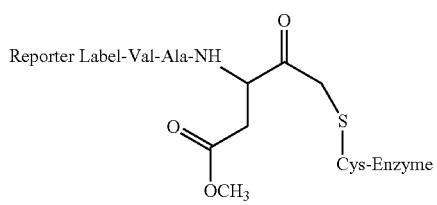

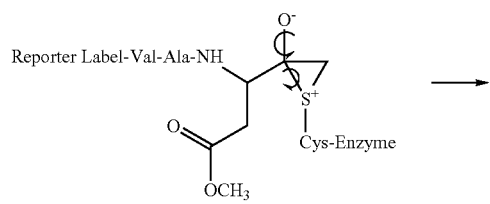

It is believed that the second intermediate rearranges to give the final stable thioether adduct, which is retained within the apoptotic cell.

The following structure is an example of an aza-peptide epoxide modification of the reactive end that is believed to bind to the cysteine residue in the catalytic site of active caspases.

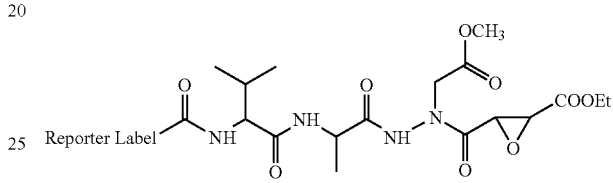

One example of a fluorescent labeled aza-peptide epoxide modified caspase ligand is a carboxyfluorescein-valanyl-alanyl-$_{aza}$aspartyl(O-methyl)-Epoxide.

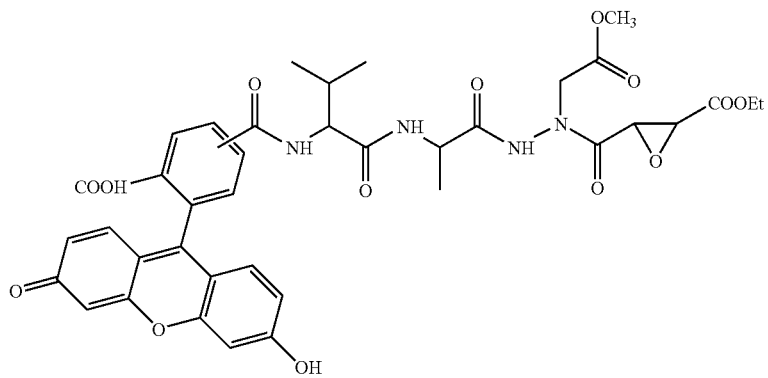

One example of a metal chelate labeled aza-peptide epoxide modified caspase ligand is a Tc-valanyl-alanyl-$_{aza}$aspartyl(O-methyl)-Epoxide.

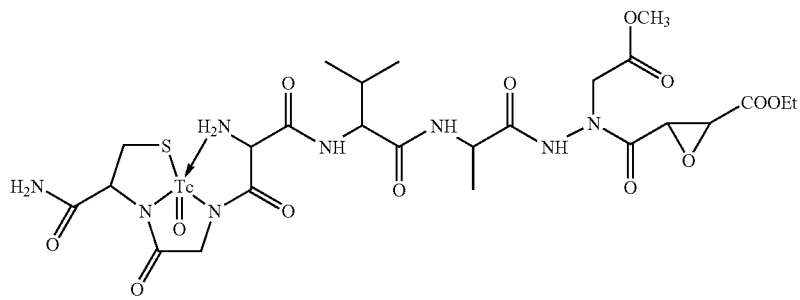

It is believed that once the aza-peptide epoxide modified peptides enter the cell and come into contact with an active caspase, the sequence is recognized by the catalytic site and forms a covalent bond where the active site cysteine nucleophilically attacks the three-member ring forming the final product that will remain in the apoptotic cell.

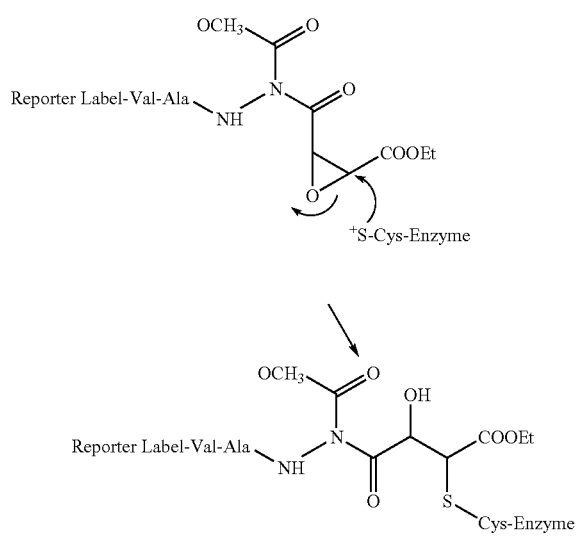

An Asp(OMe)—OPh modified reactive end is believed to bind to the cysteine residue in the catalytic site of active caspases.

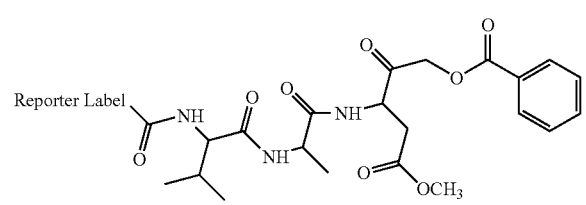

One example of a fluorescent labeled OPh caspase ligand is carboxyfluorescein-valanyl-alanyl-aspartyl(O-methyl)-benzoyloxymethyl ketone.

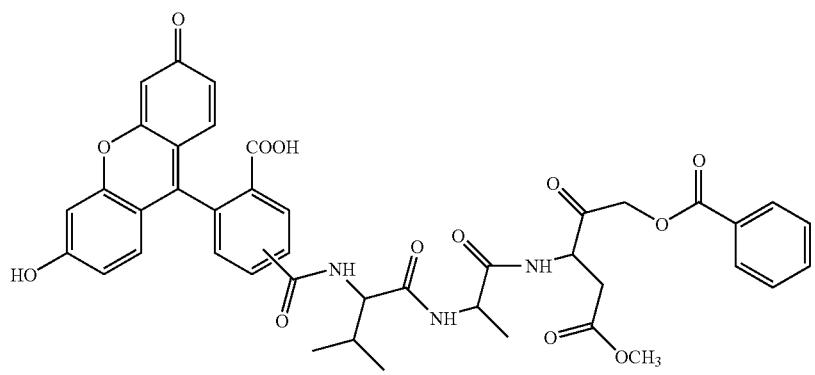

One example of a metal chelate labeled OPh caspase ligand is Tc-valanyl-alanyl-aspartyl(O-methyl)-benzoyloxymethyl ketone.

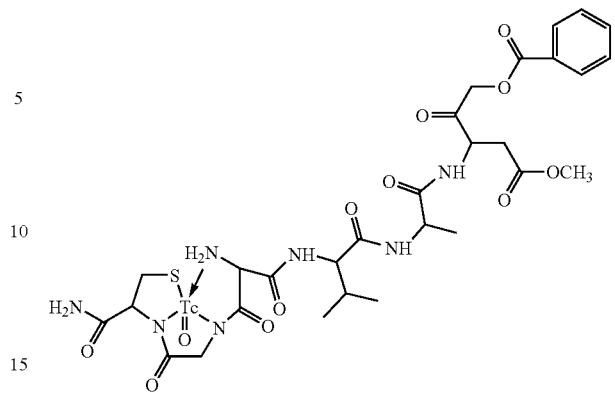

Following synthesis, the agent may be further processed into a vial by dissolving it in a suitable organic solvent such as acetone, acetonitrile, dimethylformamide (DMF), dimethylsulfoxide (DMSO), 1,4-dioxane or tetrahydrofuran. Once dissolved, the agent may then be diluted into a suitable non-aqueous or aqueous liquid and dispensed into individual vials. The individual vials may be cooled to less than 0° C., lyophilized under vacuum between 10 to 500 millitor to dryness at −80° C. to +100° C., with or without a liquid nitrogen or dry ice trap. Individual vials can then be capped and stored between −80° C. and 20° C.

The in vivo apoptosis detection and imaging kits may include one or more vials of reagent (e.g., processed and lyophilized reagent) and an appropriate Injection Buffer (e.g., a bottle of 10× Injection Buffer). A 10× Injection Buffer may be prepared according to the following recipe in endotoxin free DI $H_2O$: 87.66 g/L of NaCl (1.5 M), 60.53 g/L of $Na_2HPO_4.12H_2O$+4.84 g/L of $NaH2PO_4.2H_2O$ (0.2 M phosphate), pH 6.9.

Prior to use, the reagent may be dissolved in DMSO and may be used immediately or aliquoted and stored, e.g., at less than −20° C. The 10× Injection Buffer may be diluted 1:10 in endotoxin free DI $H_2O$ and filter sterilized resulting in a final pH of 7.4. The reagent may be diluted to injection concentrations in the sterilized 1× Injection Buffer. The reagent may be injected into the animal between 0.1 micromoles per kg and 1.0 milimoles per kg. It may then be allowed to circulate throughout the animal, e.g., for from about 5 minutes to several hours before detection and imaging of apoptosis.

Certain embodiments of the invention provide a method for in vivo determination of whether a therapeutic agent induces apoptosis in one or more viable whole cells, tissues, organs or tumors in mammals, including humans, including: 1) treating the subject with the therapeutic agent; 2) introducing a caspase affinity labeling agent into the subject; and 3) detecting the presence of the group L in the cells, tissues, organs, or tumors, wherein the presence of L correlates with the ability of the agent to induce apoptosis.

Certain embodiments of the present invention also provide a method for in vivo determination of whether a therapeutic agent reduces or inhibits apoptosis in one or more viable whole cells, tissues, organs, or tumors in mammals, including humans, including: 1) treating the subject with the therapeutic agent; 2) introducing a caspase affinity labeling agent into the subject; and 3) detecting the presence of the group L in the cells, tissues, organs, or tumors, wherein the presence of L correlates in a negative sense, with whether the therapeutic agent reduces or inhibits apoptosis.

Certain embodiments of the present invention also provide a method for in vivo determination of whether a radiation treatment induces apoptosis in one or more viable whole cells, tissues, organs, or tumors in mammals, including humans, including: 1) treating the subject with radiation; 2) introducing a caspase affinity labeling agent into the subject; and 3) detecting the presence of the group L in the cells, tissues, organs, or tumors, wherein the presence of L correlates with the ability of the agent to induce apoptosis.

Certain embodiments of the invention provide a method or in vivo determination of whether a radiation reduces or inhibits apoptosis in one or more viable whole cells, tissues, organs, or tumors in mammals, including humans, including: 1) treating the subject with the radiation; 2) introducing a caspase affinity labeling agent into the subject; and 3) detecting the presence of the group L in the cells, tissues, organs, or tumors, wherein the presence of L correlates in a negative sense, with whether the therapeutic agent reduces or inhibits apoptosis.

Certain embodiments of the invention provide an in vivo diagnostic method for determining the presence or absence of a disease characterized by the presence of apoptosis in one or more viable whole cells, tissues, organs, or tumors in mammals, including humans, including: 1) introducing a caspase affinity labeling agent into the subject; and 2) detecting the presence of the group L in the cells, tissues, organs, or tumors; wherein the presence of L correlates with the presence or absence of the disease.

Certain embodiments of the invention provide an in vivo diagnostic method to diagnose macular degeneration and proliferative retinopathy by determining the presence or absence of a disease characterized by the presence of apoptosis in one or more viable whole cells within the retina in mammals, including humans, including: 1) introducing a caspase affinity labeling agent into the subject; and 2) detecting the presence of the group L in the retina; wherein the presence of L correlates with the presence or absence of the disease.

Certain embodiments of the invention provide an in vivo diagnostic method to diagnose glaucoma by determining the presence or absence of a disease characterized by the presence of apoptosis in one or more viable retinal glial cells in mammals, including humans, including: 1) introducing a caspase affinity labeling agent into the subject; and 2) detecting the presence of the group L in the retinal glial cells; wherein the presence of L correlates with the presence or absence of the disease.

Certain embodiments of the invention provide an in vivo diagnostic method to assess the amount of damage in cardiac disease by determining the presence or absence of a disease characterized by the presence of apoptosis in one or more viable whole cells within cardiac tissue in mammals, including humans, including: 1) introducing a caspase affinity labeling agent into the subject; and 2) detecting the presence of the group L in the cardiac tissues; wherein the presence of L correlates with the presence or absence of the disease.

Certain embodiments of the invention provide an in vivo diagnostic method to assess the amount of damage in neurodegenerative disease by determining the presence or absence of a disease characterized by the presence of apoptosis in one or more viable whole cells and neurons within nerve tissue and the brain in mammals, including humans, including: 1) introducing a caspase affinity labeling agent into the subject; and 2) detecting the presence of the group L in the nerve tissues; wherein the presence of L correlates with the presence or absence of the disease.

Certain embodiments of the invention provide an in vivo method for evaluating the sensitivity of a disease in a mammal to a therapeutic agent or treatment, wherein the presence- or level of apoptotic activity correlates with the sensitivity of the disease in mammals, including humans, including: 1) subjecting the mammal to the therapeutic agent or treatment, 2) introducing a caspase affinity labeling agent into the subject; and 3) detecting the presence or abundance of the affinity labeling agent in the cells, tissues, organs, or tumors; wherein the presence or abundance correlates with the sensitivity.

Certain embodiments of the invention provide a method for the monitoring of cancer treatment, wherein the presence- or level of apoptotic activity correlates with the efficacy of the treatment in mammals, including humans, including: 1) subjecting the subject to the therapeutic agent or treatment; 2) introducing a caspase affinity labeling agent into the subject; and 3) detecting the presence or abundance of each of the affinity labeling agent in the cells, tissues, organs, or tumors; wherein the presence or abundance of apoptosis correlates with efficacy.

Certain embodiments of the invention provide a method for the monitoring of leukemia treatment, wherein the presence- or level of apoptotic activity correlates with the efficacy of the treatment in mammals, including humans, including: 1) subjecting the subject to the therapeutic agent or treatment; 2) introducing a caspase affinity labeling agent into the subject; and 3) detecting the presence or abundance of the affinity labeling agent in the bone marrow, thymus, lymph nodes, spleen and circulating blood; wherein the presence or abundance of apoptosis correlates with efficacy.

Certain embodiments of the invention provide a method for the monitoring of blood and bone marrow disease treatment, wherein the presence- or level of apoptotic activity correlates with the efficacy of the treatment in mammals, including humans, including: 1) subjecting the subject to the therapeutic agent or treatment; 2) introducing a caspase affinity labeling agent into the subject; 3) drawing blood and preparing peripheral blood monocytes (PBMCs); and 4) detecting the presence or abundance of the affinity labeling agent in the cells; wherein the presence or abundance of apoptosis correlates with treatment efficacy.

Certain embodiments of the invention provide a method for the monitoring of leukemia treatment, wherein the presence- or level of apoptotic activity correlates with the efficacy of the treatment, in mammals, including humans, including: 1) subjecting the subject to the therapeutic agent or treatment; 2) introducing a caspase affinity labeling agent into the subject; 3) drawing blood and preparing peripheral blood monocytes (PBMCs); and 4) detecting the presence or abundance of the affinity labeling agent in the cells; wherein the presence or abundance of apoptosis correlates with treatment efficacy.

Certain embodiments of the invention provide a method for determining if one or more compounds, e.g., within a chemical library, modulate caspase activity in a mammal including, contacting the mammal, including humans, with one or more compounds, and contacting the subject as with a caspase affinity labeling agent; and determining the level of the affinity labeling agent in the subject, and comparing the level of affinity labeling agent in the subject with a control subject not exposed to the compound to determine whether the compound modulated the caspase activity.

Certain embodiments of the invention provide a method for determining if one or more compounds, e.g., within a chemical library, induces apoptosis in mammals, including humans, including, contacting the subject with one or more compounds, and contacting the subject with an apoptosis affinity labeling agent; and determining the level of the affinity labeling agent in the subject, and comparing the level of affinity labeling agent in the subject with a control subject not exposed to the compound to determine whether the compound induces apoptosis.

Certain embodiments of the invention provide a method for determining if one or more compounds, e.g., within a chemical library, reduces apoptosis in mammals, including humans, including, contacting the subject with one or more compounds, and contacting the subject with an apoptosis affinity labeling agent; and determining the level of the affinity labeling agent in the subject, and comparing the level of affinity labeling agent in the subject with a control subject not exposed to the compound to determine whether the compound reduces apoptosis.

Certain embodiments of the invention provide a method for longitudinal determination if one or more compounds, e.g., within a chemical library, modulate caspase activity in a mammal including, contacting the subject as with a caspase affinity labeling agent before contacting the subject with one or more compounds; and determining the level of the affinity labeling agent in the subject, and contacting the mammal, including humans, with one or more compounds, then contacting the subject as with a caspase affinity labeling agent; and determining the level of the affinity labeling agent in the subject, and comparing the level of affinity labeling agent in the subject before exposure to the compound to determine whether the compound modulated the caspase activity.

Certain embodiments of the invention provide a method for determining if one or more compounds, e.g., within a chemical library, induces apoptosis in mammals, including humans, including, contacting the subject as with a caspase affinity labeling agent before contacting the subject with one or more compounds; and determining the level of the affinity labeling agent in the subject, and contacting the mammal, including humans, with one or more compounds, then contacting the subject as with a caspase affinity labeling agent; and determining the level of the affinity labeling agent in the subject, and comparing the level of affinity labeling agent in the subject before exposure to the compound to determine whether the compound induces caspase activity.

Certain embodiments of the invention provide a method for determining if one or more compounds, e.g., within a chemical library, reduces apoptosis in mammals, including humans, including, contacting the subject as with a caspase affinity labeling agent before contacting the subject with one or more compounds; and determining the level of the affinity labeling agent in the subject, and contacting the mammal, including humans, with one or more compounds, then contacting the subject as with a caspase affinity labeling agent; and determining the level of the affinity labeling agent in the subject, and comparing the level of affinity labeling agent in the subject before exposure to the compound to determine whether the compound reduces caspase activity.

In certain embodiments of the invention, detection is carried out using NMR, MRI, CT, CAT, PET scans, or scintigraphy; flow cytometer; a laser scanning cytometer; a fluorescence microplate reader; a luminescence microplate reader, a chromogenic microplate reader; a fluorescence microscope; a confocal microscope; a luminescence microscope; a bright-field microscope; whole animal fluorescence imaging systems (optical imaging systems); or a whole animal luminescence imaging system.

In certain embodiments of the invention, detection is carried out using a Window Chamber inserted into the test subject for direct observation.

In certain embodiments of the invention, detection is carried out using a fluorescence microscope; a confocal microscope; a bright-field microscope, or luminescence microscope.

In certain embodiments of the invention, detection is carried out and/or confirmed by removing a sample from the test subject such as by extraction, biopsy, venipuncture, dissection, or other suitable methods and detection by flow cytometer; a laser scanning cytometer; a fluorescence microplate reader; a chromogenic microplate reader; a fluorescence microscope; a confocal microscope; a bright-field microscope; a luminescence microplate reader; or a luminescence microscope.

Certain embodiments of the invention provide a kit such as an assay kit including packaging materials including 1) one or more caspase affinity labeling agents; 2) 10× injection buffer; and 3) instructions for using the compound to determine the level of apoptosis in vivo.

The invention has been described with reference to various specific and preferred embodiments and techniques. However, it should be understood that many variations and modifications may be made while remaining within the spirit, and scope, of the invention.

EXAMPLE 1

Using a mouse window chamber model, SCK mammary tumors were evaluated for levels of apoptosis induction in tumors following irradiation treatment with arsenic trioxide (ATO) and heat. A window chamber, used for viewing tumors, was placed over a fold of skin in A/J mice. $2 \times 10^5$ SCK mammary carcinoma cells were injected into the skin fold.

The tumors were allowed to grow for 7 to 9 days. In the test mice, tumors were irradiated with 20 Gy, 8 mg/kg ATO and 2 hours later the tumors were heated at 41.5° C. for 60 minutes. Control mice were not treated with irradiation or heat and a placebo was injected instead of ATO.

After allowing the tumors to grow 7 days, the test mice were first irradiated with 20 Gy. This was immediately followed by an intraperitoneal (I.P.) injection of ATO. The ATO was dissolved in water and injected in a solution of PBS with 5% w/v of dextrose at a concentration of 8 mg/kg. After 2 hours the tumors were heated at 41.5° C. for 60 minutes. Control mice received an I.P. injection of PBS with 5% dextrose.

Prior to treatment, tumors were examined in control mice and designated test mice. Low magnification bright-field image composite photographs of SCK mammary tumors taken through a window chamber reveal a low level of hemorrhaging in all tumors (FIG. 1).

Three hours post treatment, low magnification bright-field image composite photographs show continued low levels of hemorrhaging in control mice and high levels of hemorrhaging in test mice (FIG. 2) demonstrating the efficacy of the treatment. After 24 hours the control mice had the same levels of hemorrhaging and the levels of hemorrhaging continued to increase in the test mice that received the treatment (FIG. 3).

Apoptosis was detected by injecting the in vivo apoptosis detection reagent FAM-VAD-FMK into the tail vein of control and test mice. A processed vial of reagent containing 52 µg of FAM-VAD-FMK was dissolved into 50 µL of DMSO. This solution was diluted by adding 200 µL of sterile 1× injection buffer. Of the diluted reagent, 40 µL (8.3 µg) was injected I.V. through the tail vein and allowed to circulate in the mouse for 30 minutes. The level of apoptosis in each tumor was viewed directly through the window chambers at high magnification with an excitation wavelength of 488 nm and using a FITC filter.

Control mice were given FAM-VAD-FMK injections following placebo injections. These mice showed a low level of apoptosis, as would be expected in a fast growing tumor (FIG. 4). Test mice that received ATO treatment were given FAM-VAD-FMK injections at 3 hours and 24 hours after ATO treatment, and apoptosis was evaluated as before. After 3 hours, there was a substantial increase in the level of apoptosis, as seen in FIG. 5. The level of apoptosis was even higher after 24 hours (FIG. 6).

In another set of mice, the tumors were allowed to grow for 7 days. Control mice received placebo injections as before and test mice received ATO injections as before. After 24 hours all mice received I.V. injections of FAM-VAD-FMK as before. The in vivo apoptosis detection and imaging reagent was allowed to circulate through each mouse for 30 minutes. After imaging tumor-associated apoptosis in vivo, tumor tissue was collected from the window chamber by scraping the tumor out of the chamber into a trypsin solution, stirring for 30 minutes with 10 µg/ml DNase and 5 µg/ml collagenase, filtering the suspension using a 70 µM cell strainer. Flow cytometry was then performed using a FACS Caliber flow cytometer (Becton Dickinson Immunocytometry System, San Jose, Calif.) for the analysis of apoptosis in the cell population obtained from the window chamber. All data was acquired with an event acquisition set for 10,000 events. Data was analyzed using CellQuest Pro cytometer software. The results indicated a two-fold increase in apoptosis with the control mouse having 18% apoptotic cells and the test mouse having 39% apoptotic cells (FIG. 7).

EXAMPLE 2

A longitudinal study was performed in nu/nu mice to assess the efficacy of arsenic trioxide (ATO) on FSaII murine fibrosarcoma tumors before and after ATO treatment through a window chamber.

Dorsal skin flap chambers (DSFC) were surgically implanted into the backs of nu/nu mice as follows. Entire implantation procedure was conducted within a laminar flow hood to preserve a sterile field. Skin was washed twice with betadine and allowed to dry. One sterilized chamber piece containing a round window (9 mm) was placed on one side of the dorsal skin fold. Holes for three connecting screws were made through the skin fold connecting with another chamber piece with a similar window. The assembly was then tightened together with screws and nuts through the chamber piece spacers. A circle of cutaneous tissue and fascia was carefully cut away from the skin fold inside the DSFC window, exposing the blood vessels of the subcutaneous tissue adjacent to the striated muscles of the opposing skin fold. Antibiotic ointment (bacitracin zinc/polymyxin B sulfate/neomycin sulfate) was used on the edges of the wound inside the DSFC window. A glass window was placed in the chamber to cover the exposed tissue and secured with a snap C-ring. The surgical wound procedure was then repeated in the opposite DSFC window so that a very thin, transparent layer of fascia and vessels remained visible through both windows (created to facilitate microscope light transmission through the tissue). Finally, the chamber was sutured to the skin.

After surgery, the animals were housed in barrier cages inside a humidified incubator maintained at 32° C. with unrestricted access to food and water. To minimize risk of infection, all mice were given amoxicillin in their drinking water (250 mg per 5 mL water) after DSFC implantation and throughout the experiment.

Tumor cells were implanted into one side of the chamber by temporary removal of the C-ring and glass cover slip. $1 \times 10^5$ FSaII murine fibrosarcoma tumor cells in 10 µL Matrigel (BD Biosciences, Bedford, Mass.) were added on top of the fascia and the window closed back over the tissue as described above. Cells were placed within the chamber 24 hrs post surgery. Mice were checked daily for general health as well as for vessel presence, tumor progression and chamber-skin interaction. Images were taken of the tumor by removing the C-ring and glass cover slip and attaching the chamber of the anesthetized mouse to a modified microscope stage.

Anti-vascular agent and administration: Arsenic trioxide (ATO) was originally obtained from Cell Therapeutics, Inc. (Seattle, Wash.) under the brand name, Trisenox, at a concentration of 1.0 mg/mL. Mice to be injected were weighed and ATO was injected IP at a dose of 8.0 mg ATO per kilogram of mouse body weight.

In vivo apoptosis detection reagent carboxyfluorescein-valanyl-alanyl-aspartyl(O-methyl)-fluoromethyl ketone (FAM-VAD-FMK), preparation and administration: A processed vial of reagent containing 52 µg of FAM-VAD-FMK was dissolved into 50 µL of DMSO. This solution was diluted by adding 250 µL of sterile 1× injection buffer. Of the diluted reagent, 70 µL (12.0 µg) was injected IV through the tail vein and allowed to circulate in the mouse for 45 minutes. The level of apoptosis in each tumor was viewed directly through the window chambers at 10× magnification with an excitation wavelength of 488 nm and using a FITC filter.

Results: The tumors were allowed to grow for 9 days. FAM-VAD-FMK was injected and allowed to circulate for 45 minutes. The DFSC C-ring and glass cover were removed and the mouse was connected to the microscope. A 10× photograph was taken using a 488 nm excitation with a FITC filter (FIG. 8). This photograph shows a lack of apoptosis occurring in the tumor. The same mouse was then injected with ATO as described above. The ATO was allowed to work for 3 hours before the mouse was injected a second time with FAM-VAD-FMK. After 45 minutes the mouse was again connected to the microscope and the same tumor was photographed (FIG. 9). This photograph shows a significant level of apoptosis in the mouse tumor.

Final conclusion: The IV injection of a in vivo apoptosis detection reagent (FAM-VAD-FMK) works for the in vivo detection of apoptosis in living tissue in an animal. It can also be used to perform longitudinal studies in the same animal with no side-effects from the reagent. This method represents a new and valuable method to reliably demonstrate anti-cancer drug activity in living normal or malignant tissue.

EXAMPLE 3

The objective of this project was to develop an in vivo animal model for the detection of morphine-mediated apoptosis. Drugs of abuse, including morphine, have been shown to induce apoptosis in cultured cells. Apoptosis is initiated through a variety of complex pathways that lead to the activation of cysteine proteases known as caspases. The detection of apoptosis is important for the understanding of the adverse effects of drugs, e.g., drugs of abuse, e.g., morphine. Although there are techniques for the detection of apoptosis, those techniques are generally limited to removing the cells from their natural environment. This mechanical processing is known to induce apoptosis, potentially resulting in exaggerated positive results. The objective of this study was to develop an in vivo model for the detection of apoptosis induced by morphine.

To test the effects of morphine, the mice were divided into 4 groups, dependent on the treatment. One group received a placebo, a second group received LPS to stimulate cells, a third group received morphine, and a fourth group received morphine and LPS. After the mice were given their respective treatments, they received IV injections of FAM-VAD-FMK. A processed vial of reagent containing 52 μg of FAM-VAD-FMK was dissolved into 50 μL of DMSO. This solution was diluted by adding 200 μL of sterile 1× injection buffer. Of the diluted reagent, 40 μL (8.3 μg) was injected IV through the tail vein and allowed to circulate in the mouse for 45 minutes. Spleen, Liver, Thymus, and CNS tissues were isolated from different treatment groups, frozen and mounted on glass slides. The various cell types were adjusted to $1\times10^6$ cells/mL and cytospun on a glass slide for analysis by fluorescence microscopy. Sections were photographed and analyzed by MetaMorph analysis program for apoptosis positive cell counts. Counts were analyzed by statistics software. Morphine statistically enhanced LPS induced apoptosis in the Spleen and Thymus (p=0.012 and 0.0018 respectively). An increase in apoptosis was detected in the liver and central nervous system, however, they were not statistically significant. Morphine alone did not induce apoptosis. Quantitative results are summarized in Table 1.

Conclusion: In contrast to previously published reports on morphine mediating in vitro apoptosis of immune cells, this study demonstrates that morphine alone did not significantly induce apoptosis. However, morphine did enhanced apoptosis of LPS activated cells detected in spleen, bone marrow and liver tissues.

Table 1 is a summary of quantitative results of apoptosis induced by LPS, morphine, and morphine+LPS in the spleen, thymus, liver and CNS. In vivo apoptosis detection was made by intravenous injection of 8.3 μg of FAM-VAD-FMK with a 45 minute incubation time. Spleen, Liver, Thymus, and CNS tissues were isolated from different treatment groups, frozen and mounted on glass slides. Sections were photographed and analyzed by MetaMorph analysis program for apoptosis positive cell counts. Counts were analyzed by statistics software.

TABLE 1

| Tissues | Treatments | Animals | Counts |
| --- | --- | --- | --- |
| Spleen | Placebo | 1/4 | 26 |
|  | Morphine | 2/4 | 39 ± 12 |
|  | LPS | 3/4 | 48 ± 6 |
|  | Morphine + LPS | 4/4 | 117 ± 23* |
| Liver | Placebo | 1/4 | 11 |
|  | Morphine | 3/4 | 12 ± 3 |
|  | LPS | 3/4 | 17 ± 5 |
|  | Morphine + LPS | 4/4 | 78 ± 16 |
| Thymus | Placebo | 0/4 | 0 |
|  | Morphine | 2/4 | 12 ± 6 |
|  | LPS | 2/4 | 21 ± 7 |
|  | Morphine + LPS | 4/4 | 103 ± 13* |
| CNS | Placebo | 0/4 | 0 |
|  | Morphine | 0/4 | 0 |
|  | LPS | 1/4 | 6.5 |
|  | Morphine + LPS | 2/4 | 22.5 ± 28 |

DOCUMENTS

Bedner, E., Smolewski, P., Amstad, P., and Darzynkiewicz, Z. (2000) Activation of caspases measured in situ by binding of fluorochrome-labeled inhibitors of caspases (FLICA): correlation with DNA fragmentation. Exp. Cell Res. 259, 308-313.

Belhocine, T., Steinmetz, N. L I, C., Green, Blankenberg, F. G. (2004) The imaging of apoptosis with the radiolabeled annexin V: optimal timing for clinical feasibility. Technol Cancer Res Treat 3(1), 23-32.

Boersma, H. H., Kietselaer, B. L., Stolk, L. M., Bennaghmouch, A. Hofstra, L., Narula, J., Heidendal, G. A., Reutelingsperger, C. P. (2005) Past, present, and future of annexin A-5: from protein discovery to clinical applications. J Nuc Med 46(12), 2035-2050.

Corsten, M. F., Hofstra, L., Narula, J., and Reutelingsperger, C. P, M. (2006) Counting heads in the war against cancer: defining the role of annexin A5 imaging in cancer treatment and surveillance. Cancer Res 66, 1255-1260.

Dicker, D. T., Kim, S. H., Jin, Z., and El-Deiry, W. S. (2005) Heterogeneity in non-invasive detection of apoptosis among human tumor cell lines using annexin-V tagged with EGFP or Qdot-705. Cancer Biol. Ther., 9, 1014-1017.

Dillon, S. R., Constantinescu, A., and Schlissel, M. S. (2001) Annexin V binds to positively selected B cells. J of Immunol 166, 58-71

Ekici, O. D., Gotz, M. Gg, James, K. Ee., Li, Z. Z., Rukamp, B. J., Asgian, J. L., Caffrey, C. R., Hansell, E., Dvorak, J., McKerrow, J. H., Potempa, J., Travis, J., Mikolajczyk, J., Salvesen, G. S., and Powers, J. C. (2004) Aza-peptide Michael acceptors: a new class of inhibitors specific for caspases and other clan CD cysteine proteases. J. Med. Chem. 47(8)1889-1892.

Kietselaer B. L. J. H., Hofstra, L, Dumont, E. A. W. J., Reutelingsperger, C. P., and Heidendal, G. A. (2003) The role of labeled Annexin A5 in imaging of programmed cell death. From animal to clinical imaging. Q J Nucl Med, 47(4), 349-361.

Krantz, A., Copp, L. J., Coles, P. J., Smith, R. A., Heard, S. B. (1991) Peptidyl (acyloxy)methyl ketones and the quiescent affinity label concept: the departing group as a . . . . Biochemistry 30, 4678-4687.

Reddy, G. K. (2005) Noninvasive visualization of apoptosis using radiolabeled annexin V could predict response to chemotherapy. Clin Lung Cancer 7(3), 166-167.

Smolewski, P., Bedner, E., Du, L., Hsieh, T. Wu, J. M., Phelps, D. J., and Darzynkiewicz, Z. (2001) Detection of caspases activation by fluorochrome-labeled inhibitors: Multiparameter analysis by laser scanning cytometry. Cytometry 44, 73-82.

Smolewski, P., Grabarek, J., Lee, B. W., Johnson, G. L., and Darzynkiewicz, Z. (2002) Kinetics of HL-60 cell entry to apoptosis during treatment with TNF-α or camptothecin assayed by the stathmo-apoptosis method. Cytometry 47, 143-149.

Thornberry, N. A., Peterson, E. P., Zhao, J. J., and Howard, P. R. (1994) Inactivation of interleukin-1beta converting enzyme by peptide (acyloxy)methyl ketones. Biochemistry 33, 3934-3940.

Vanderheyden, J. L., Liu, G., He, J., Patel, B., Tait J. F., and Hnatowich, D. J. (2006) Evaluation of 99m Tc-MAG3-annesin V: influence of the chelate on in vitro and in vivo properties in mice. Nucl Med Biol 33(1), 135-144.

Watanabe, H., Murata, Y., Miura, M., Hasegawa, M. Kawamoto, T., and Shibuya, H. (2006) In vivo visualization of radiation-induced apoptosis using 125I-annexin V. Nucl Med Commun 27(1), 81-89.

U.S. Patent Application Publication 2005/0244812 A1
U.S. Patent Application Publication 2005/0276750 A1
U.S. Pat. No. 7,056,947 B2

All publications and patent documents cited herein are incorporated by reference herein, as though individually incorporated by reference.

The invention has been described with references to various specific and preferred embodiments and techniques. However, it should be understood that many variations and modifications may be made while remaining within the spirit and scope of the invention.

retinopathy, wherein the caspase affinity labeling agent is a compound of formula I:

$$L_1\text{-}A_1\text{-}X_1\text{---}NH\text{---}CH(R_1')C(=O)CH_2F \quad (I)$$

wherein:
L$_1$ is a detectable group;
A$_1$ is a direct bond or a linker;
X$_1$ is absent, an amino acid, or a peptide; and
R$_1$' is an aspartic acid side-chain, an ester of aspartic acid, an aza-peptide epoxide modification of the aspartic acid, an aza-peptide Michael acceptor, an aldehyde modification of the aspartic terminal carboxyl group, a chloromethyl ketone group, a fluoromethyl ketone group, OPh, or an acyloxy reactive group.

2. The method of claim 1, wherein the disease is a retinal disease.

3. The method of claim 1, wherein detection is carried out using NMR, MRI, CT, CAT, PET scan, sctintigraphy, a flow cytometer, a laser scanning cytometer, a fluorescence microplate reader, a luminescence microplate reader, a chromogenic microplate reader, a fluorescence microscope, a confocal microscope, a luminescence microscope, a bright-field microscope, a whole animal fluorescence imaging system, a whole animal luminescence imaging system, or a combination thereof.

4. The method of claim 1, wherein detection is carried out using a window chamber that has been inserted into the animal.

5. The method of claim 4, wherein detection is carried out using a fluorescence microscope, a confocal microscope, a bright-field microscope, or a luminescence microscope.

6. The method of claim 1, wherein the presence or abundance of the affinity labeling agent is detected in one or more viable cells within the retina of the animal.

7. The method of claim 1, wherein the presence or abundance of the affinity labeling agent is detected in one or more viable retinal glial cells.

8. The method of claim 1, wherein the caspase affinity labeling agent is introduced into the animal by intravenous,

What is claimed is:

1. An in vivo diagnostic method for determining the presence or absence of a disease of the eye characterized by the presence of apoptosis, comprising detecting the presence of at least one cell permeant caspase affinity labeling agent in cells of the eye of an animal into which the at least one cell permeant caspase affinity labeling agent has been introduced, wherein the presence or absence of the at least one cell permeant caspase affinity labeling agent correlates with the presence or absence of the disease of the eye, wherein the disease of the eye is glaucoma, macular degeneration, or proliferative intravascular, intraperitoneal, intravitreal, intraocular, intracranial, intrapleural, intrathoracic, intramuscular, intrapulmonary, injection, perfusion, or lavage administration.

9. The method of claim 1, wherein the animal is a mammal.

10. The method of claim 9, wherein the mammal is a human.

11. The method of claim 1, wherein the detectable group is a Lanthanide series element.

12. The method of claim 1, wherein the detectable group is a positron emitter.

13. The method of claim 1, wherein the detectable group is a fluorescent label.

14. The method of claim 1, wherein the detectable group is a radioisotope.

15. The method of claim 1, wherein the detectable group is Gd, Tb, Eu, Ce, Pr, Nd, Pm, Sm, Dy, Ho, Er, Tm, Yb, Lu, Fe, Mn, Re, and Tc, I Ba, $^{11}$C, $^{13}$N, $^{15}$O, $^{64}$Cu, a fluorescein, a sulforhodamine, a Cy dye, a BODIPY, a coumarin, $^{3}$H, $^{14}$C, or $^{35}$S.

16. The method of claim 1, wherein $X_1$ is the amino acid or amino acid sequence V, VA, YVA, DEV, LEE, LEH, VDVA (SEQ ID NO:1), IET, WHE, AEV, A, V, or E.

17. The method of claim 1, wherein $R_1'$ is $CH_2$—COOH, or —$CH_2CO_2R$, wherein R is $C_1$-$C_6$ alkyl or benzyl, $CH_3$, $C_2H_5$ or $CH_2C_6H_5$.

18. The method of claim 1, wherein the caspase affinity labeling agent is carboxyfluorescein-valanyl-alanyl-aspartyl (O-methyl)-fluoromethyl ketone.

19. The method of claim 1, wherein the caspase affinity labeling agent binds covalently to the active catalytic site of a caspase and is retained within the cell.

20. The method of claim 1, wherein the disease is glaucoma.

21. The method of claim 1, wherein the disease is macular degeneration.

22. The method of claim 1, wherein the disease is proliferative retinopathy.

23. The method of claim 8, wherein the caspase affinity labeling agent is introduced into the animal by intravenous administration.

* * * * *